(12) United States Patent
Pompa

(10) Patent No.: US 9,604,215 B2
(45) Date of Patent: Mar. 28, 2017

(54) THIN FILM ENVELOPE

(71) Applicant: Premier Lab Supply Inc., Port St. Lucie, FL (US)

(72) Inventor: Donato Pompa, Port St Lucie, FL (US)

(73) Assignee: Premier Lab Supply Inc., Port St. Lucie, FL (US)

( * ) Notice: Subject to any disclaimer, the term of this patent is extended or adjusted under 35 U.S.C. 154(b) by 100 days.

(21) Appl. No.: 14/843,187

(22) Filed: Sep. 2, 2015

(65) Prior Publication Data

US 2017/0056875 A1    Mar. 2, 2017

(51) Int. Cl.
*B01L 3/00*        (2006.01)
*G01N 23/22*       (2006.01)

(52) U.S. Cl.
CPC .......... *B01L 3/508* (2013.01); *G01N 23/2204* (2013.01)

(58) Field of Classification Search
CPC ...... B02L 3/508; G01N 23/2204; G01N 1/20; G01N 1/12; G01N 1/08; B01L 3/505; B01L 2300/0816; B01L 9/06; B01L 3/0825
USPC ........... 73/864.91, 863, 864.51, 864, 864.64; 422/500, 560, 561, 568
See application file for complete search history.

(56) References Cited

U.S. PATENT DOCUMENTS

| 6,009,766 A     | * | 1/2000 | Solazzi | ............. | B01L 3/508 422/547 |
| 2007/0189933 A1 | * | 8/2007 | Solazzi | ............. | B01L 3/508 422/400 |
| 2011/0024434 A1 | * | 2/2011 | Pompa   | ............. | B01L 9/06 220/600 |

* cited by examiner

*Primary Examiner* — Lisa Caputo
*Assistant Examiner* — Nigel Plumb
(74) *Attorney, Agent, or Firm* — Joseph Beckman

(57) ABSTRACT

This invention relates to the design, construction and method of use of a novel thin film transport and applicator for use on XRF sample cups.

18 Claims, 2 Drawing Sheets

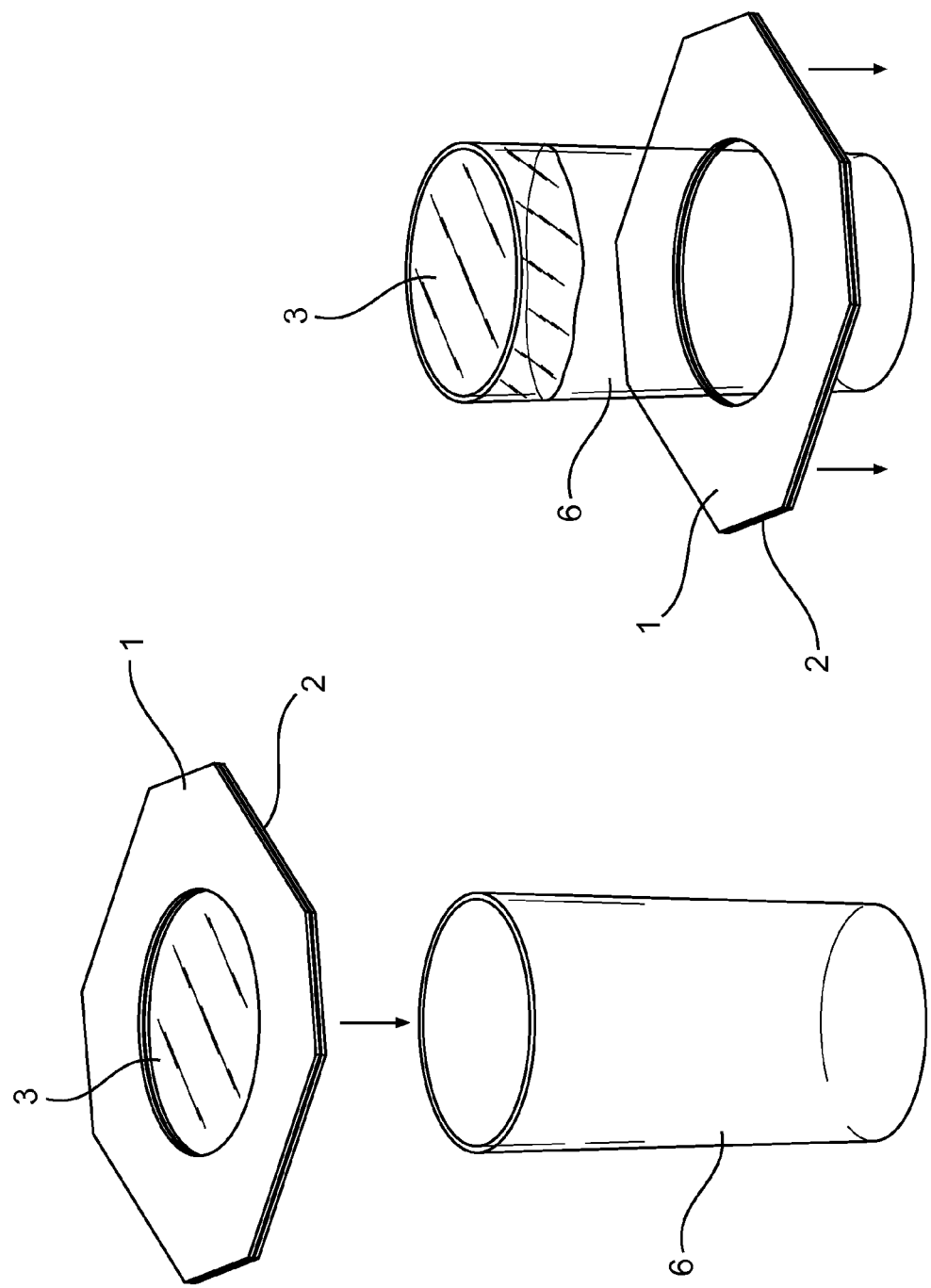

THIN FILM ENVELOPE

FIELD OF THE INVENTION

This invention relates to the design, construction and method of use of a novel thin film transport and applicator (envelope) for use on XRF sample cups.

BACKGROUND OF THE INVENTION

The present invention describes a transport and applicator to hold and apply thin film membranes to XRF sample cups.

Spectroscopic analysis (XRF Spectroscopy) utilizes sample cups to contain liquid or powder samples for elemental analysis. Sample cups generally have a thin transparent film bottom and may include a top end formed integral with the cup body known as a single ended design. Alternatively, the sample cup may include a second thin film or be secured at the top end, known as a double open end design. Sample cups are generally delivered to the analyst in parts comprised of a side wall member and complementary secondary member, which members are assembled in combination with a separate thin film component to construct a single sample cup. The sample cup, with its liquid or powder sample contained therein, is then manually transported to an XRF instrument and placed in a holder, thin film bottom down, for analysis.

Prior art thin film has traditionally been available as pre-cut squares or circles sized to cover a sample cup opening or on pre-perforated sheets. This thin film product is generally held on a substrate or interleaf of paper to facilitate handling, static control and application to the sample cup. Such products, however, are not ideal as portions of the thin film remain subject to contamination and static handling issues when attempting to secure the thin film to a sample cup. Furthermore, the thin, non-rigid nature of the product increases the difficulty of handling the product and proper placement on a sample cup without introducing error through placement, wrinkles and creases in the thin film (surface damage), contamination or easy separation of the thin film from the substrate (interleaf) on application.

Another product, as described in U.S. Pat. No. 6,009,766, introduces a carrier frame, consisting of a substrate with a through hole. A thin film is bonded to the substrate. This product is then placed over a sample cup, with the exposed thin film centered over the sample cup. The product requires perforations in the thin film product along the perimeter of the through hole to facilitate separation of the thin film on assembly of the sample cup. While this product introduces a rigid carrier assembly, the mechanism of applying the thin film to the sample cup through the use of perforations and tearing of the thin film on application has serious disadvantages solved by the present invention. The use of perforations affects the structural integrity of the thin film, providing points of stretch and unequal shear forces potentially contributing to inaccurate specimen readings, depending upon the consistency of application. The necessity of perforations to effectuate a separation upon sample cup assembly also introduces complexity in the product design avoided by the present invention. Further, the need to substitute thin films of various properties, or to dimension the frame, through hole and film to accommodate different sample cup designs requires substantial changes in manufacturing the perforated thin film product design. A different thickness film, or film of different mechanical properties will require adaptations in the perforation process or design. Finally, mechanical bonding of the thin film to the carrier frame introduces further complexity into the manufacturing process, serves to disrupt the thin film integrity and offers greater potential to introduce contaminants to the thin film surface during manufacturing or in the application of the product. The present invention avoids these disadvantages, being easily scalable both as to frame and through hole but also in the properties of the thin film.

In view of the prior arts' shortcomings, it is thus desirable to create a thin film transport and applicator which facilitates contaminant-free handling of thin film and contaminant-free application of thin film to the sample cup assembly. It is further desirable that the transport and application system allow transfer of the thin film and its subsequent assembly to occur easily and without any damage to the surface of the thin film to ensure error free XRF analytical testing results of the sample.

BRIEF DESCRIPTION OF THE DRAWINGS

FIGS. 1-4B are various views (elevations) of one embodiment of the thin film applicator (envelope).

Figure 1:
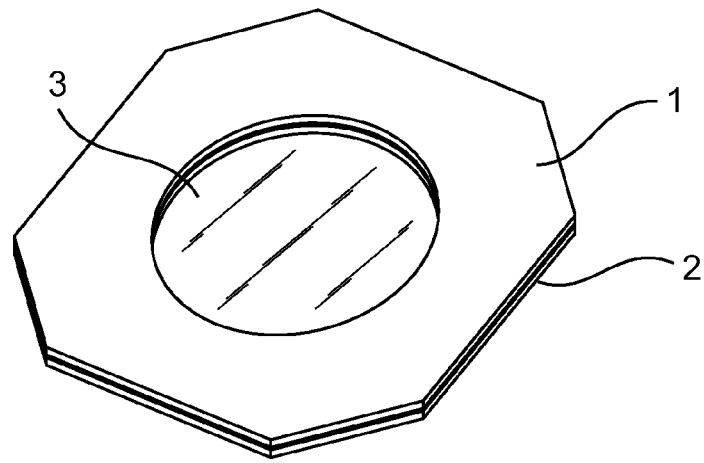

DETAILED DESCRIPTION OF THE INVENTION:

Shown in FIG. 1 is a top view of the thin film applicator (envelope) evidencing the top frame (1) with the thin film (3) situated below, and sandwiched between top frame (1) and bottom frame (2). Top frame and bottom frame are preferably structurally identical or equivalent however, dimensional and material differences may be employed to maximize manufacturing efficiencies and/or end user handling. The frame materials may be any suitable material with preferred materials being a plastic of the polyester, polypropylene or polystyrene families. The thin film may be of any suitable material conducive to the particular XRF Spectroscopic testing being conducted. Ideally, the frame material and thin film materials will both comprise plastic materials of a complementary nature which maximizes electrostatic bonding forces to assist in retention of the thin film between the top frame and bottom frame. A polystyrene frame combined with polyester thin film is one optimum combination.

Figure 2:
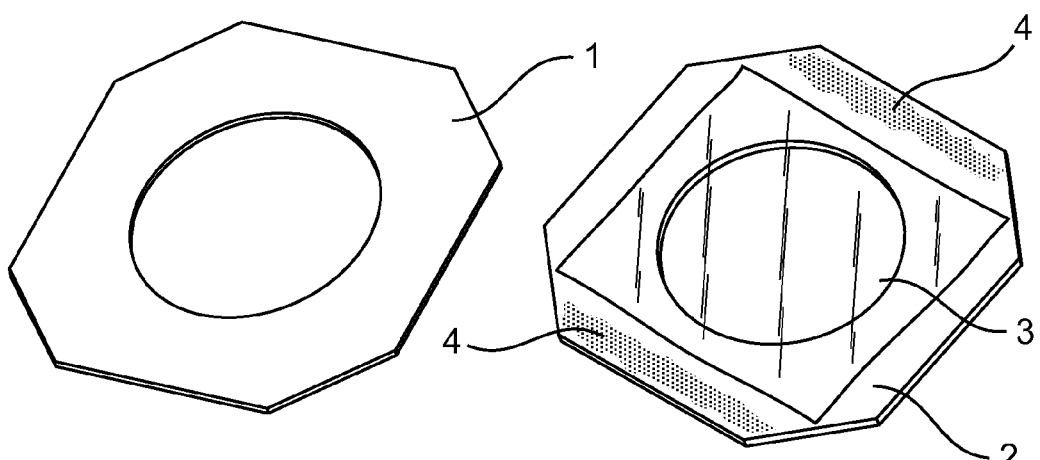

FIG. 2 shows top frame (1) separated from the thin film (3) in place on bottom frame (2). A mechanism (4) to adhere or bond the top frame (1) to bottom frame (2) is shown in place along two parallel edges of a frame. Such mechanism may be an adhesive, glue, ultrasonic welding or the application of heat (such as by a laser or heat gun) to the top frame and/or bottom frame to facilitate adherence of the two frames. Alternatively, the top frame (1) and bottom frame (2) may be formed integral along a single edge and folded to present that configuration shown in FIG. 1. FIG. 2 also shows that the mechanism (4) does not intrude upon, contact, adhere to or bond, the thin film (3). The thin film is retained between the top frame and bottom frame via electrostatic forces or a structural pattern on the inner surface of one or both of the top frame and bottom frame. In this manner, the integrity of the thin film, both structurally and with respect to the introduction of contaminants, is superior to the prior art.

Figure 3:
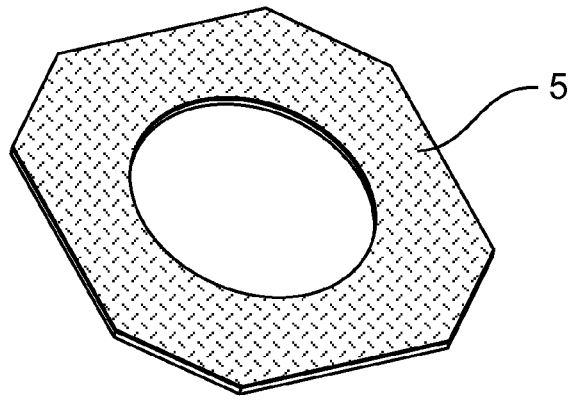

FIG. 3 shows a representative top frame (1) or bottom frame (2) having a pattern (5), structurally or visually, upon its surface. This pattern may be on the outer surface of said top frame or bottom frame (the outer surface being that surface visible after assembly) and/or this pattern may be on the inner surface of said top frame or bottom frame (the inner surface being that surface not visible after assembly). The pattern may be on either the top frame or bottom frame or the pattern may be on both the top frame and bottom frame. This pattern may include ridges or raised surfaces to facilitate product handling, rigidity and/or thin film retention. This pattern may also be visual, constituting writing or graphics designs for aesthetic purposes or for purposes of identifying the particular product, thin film content or manufacturer/reseller.

FIGS. 4A and 4B show the application of the thin film applicator (envelope) to a representative sample cup (6). In FIG. 4A the applicator (envelope) is situated according to the drawing, with the thin film (3) exposed in the top frame (1) and bottom frame (2) centered over the sample cup (6). The applicator (envelope) is then moved down over the sample cup opening as indicated in FIG. 4B, wherein the thin film (3) separates from the applicator top frame (1) and bottom frame (2) assembly.

While the dimensions and shape of the frames are not specifically defined and/or discussed herein, it is understood that such dimensions and shape may be adjusted or modified to meet industry needs or requirements without digressing from the spirit of the invention.

What is claimed:

1. An apparatus for mounting a thin-film of material across an open end of a sample cup, said thin film for retaining a sample to be analyzed spectrochemically, said apparatus comprising:
   a top frame having a through hole;
   a bottom frame having a through hole;
   a thin film material positioned between said top frame and said bottom frame and covering said through hole;
   said top frame and said bottom frame assembled by a mechanism to bond said top frame to said bottom frame along two parallel edges;
   wherein said mechanism is not in contact with said thin film material; and
   wherein said thin film material is not bonded to said top frame or said bottom frame; and
   wherein, application of said apparatus over an open end of a sample cup so that said thin film material engages the sample cup and extends across the open end thereof causes said thin film material to separate from said top frame and bottom frame assembly.

2. The apparatus of claim 1 wherein said thin film is retained between said top frame and said bottom frame by electrostatic forces.

3. The apparatus of claim 1 wherein said thin film is retained between said top frame and said bottom frame by a structural pattern upon the inner surface of said top frame and/or said bottom frame.

4. The apparatus of claim 1 wherein said top frame and said bottom frame material are selected from the group consisting of polyester, polypropylene, polystyrene, polymide and polyimide.

5. The apparatus of claim 4 wherein said mechanism is accomplished by means of a laser to bond said top frame to said bottom frame.

6. The apparatus of claim 1 wherein said mechanism is accomplished by means of a laser to bond said top frame to said bottom frame.

7. The apparatus of claim 1 wherein said top frame or said bottom frame material includes a structural or visual pattern upon its outer surface.

8. A method for mounting a thin film of material across an open end of a sample cup used for retaining a sample to be analyzed spectrochemically, said method comprising the steps of:
   providing an apparatus comprising a top frame having a through hole, a bottom frame having a through hole and a thin film positioned and retained between said top frame and said bottom frame so that said thin film covers said through hole;
   situating said apparatus onto an open end of a sample cup so that said thin film extends across said open end of said sample cup; and
   moving said apparatus down over said open end of said sample cup, wherein the said thin film separates from the top frame and bottom frame.

9. The method of claim 8 wherein said top frame and said bottom frame are assembled by a mechanism to bond said top frame to said bottom frame along two parallel edges.

10. The method of claim 9 wherein said mechanism is not in contact with said thin film material.

11. The method of claim 10 wherein said thin film material is not bonded to said top frame or said bottom frame.

12. An apparatus for mounting a thin-film of material across an open end of a sample cup, said thin film for retaining a sample to be analyzed spectrochemically, said apparatus consisting of:
   a top frame having a through hole;
   a bottom frame having a through hole;
   a thin film material positioned between said top frame and said bottom frame and covering said through hole;
   said top frame and said bottom frame assembled by a mechanism to bond said top frame to said bottom frame along two parallel edges;
   wherein said mechanism is not in contact with said thin film material; and
   wherein said thin film material is not bonded to said top frame or said bottom frame; and
   wherein, application of said apparatus over an open end of a sample cup so that said thin film material engages the sample cup and extends across the open end thereof causes said thin film material to separate from said top frame and bottom frame assembly.

13. The apparatus of claim 12 wherein said thin film is retained between said top frame and said bottom frame by electrostatic forces.

14. The apparatus of claim 12 wherein said thin film is retained between said top frame and said bottom frame by a structural pattern upon the inner surface of said top frame and/or said bottom frame.

15. The apparatus of claim 12 wherein said top frame and said bottom frame material are selected from the group consisting of polyester, polypropylene, polystyrene, polymide and polyimide.

16. The apparatus of claim 15 wherein said mechanism is accomplished by means of a laser to bond said top frame to said bottom frame.

17. The apparatus of claim 12 wherein said mechanism is accomplished by means of a laser to bond said top frame to said bottom frame.

18. The apparatus of claim 12 wherein said top frame or said bottom frame material includes a structural or visual pattern upon its outer surface.

* * * * *